United States Patent [19]

Kambara et al.

[11] Patent Number: 5,861,252

[45] Date of Patent: Jan. 19, 1999

[54] METHOD OF ANALYSIS OR ASSAY FOR POLYNUCLEOTIDES AND ANALYZER OR INSTRUMENT FOR POLYNUCLEOTIDES

[75] Inventors: Hideki Kambara, Hachioji; Kazunori Okano, Shiki; Chihiro Uematsu, Kokubunji, all of Japan

[73] Assignee: Hitachi, Ltd., Tokyo, Japan

[21] Appl. No.: 758,220

[22] Filed: Nov. 27, 1996

[30] Foreign Application Priority Data

Nov. 30, 1995 [JP] Japan .................................. 7-311949

[51] Int. Cl.⁶ .............................. C07K 3/14; C12Q 1/68; C12P 19/34; C07H 21/04

[52] U.S. Cl. ........................ 435/6; 204/182.8; 435/91.51; 435/91.1; 435/91.52; 435/91.53; 435/91.2; 536/24.3; 536/25.31; 536/25.32

[58] Field of Search ................................ 435/91.1, 91.51, 435/91.52, 91.53, 6, 91.2; 536/25.31, 25.32, 24.3; 204/182.8

[56] References Cited

U.S. PATENT DOCUMENTS

| | | | |
|---|---|---|---|
| 5,043,272 | 8/1991 | Hartley | 435/91 |
| 5,126,239 | 6/1992 | Livak et al. | 435/6 |
| 5,376,526 | 12/1994 | Brown et al. | 435/6 |
| 5,650,274 | 7/1997 | Kambara et al. | 435/6 |

OTHER PUBLICATIONS

Straus et al. Genomic subtraction for cloning DNA corresponding to deletion mutations, Proc. Natl. Acad. Sci. USA. vol. 87, pp. 1889–1893, 1990.

Genomics, 23, 1994, Murakawa et al, pp. 379–389.

DNA Sequence—J. DNA Sequencing and Mapping, vol., 2, 1991, Okubo et al, pp. 137–144.

Nature, vol. 357, Jun. 11, 1992, Mitsuhashi et al, pp. 519–520.

*Primary Examiner*—Kenneth R. Horlick
*Assistant Examiner*—Joyce Tung
*Attorney, Agent, or Firm*—Fay, Sharpe, Beall, Fagan, Minnich & McKee

[57] ABSTRACT

A method of analysis or assay for nucleotides comprises: (1) a step of digesting DNA with a restriction enzyme; (2) a step of discriminating a difference in sequences of the DNA fragments obtained in step (1) above around the 3' termini thereof with a DNA probe and extending the DNA probe by a complementary strand synthesis to fractionate the DNA fragments into groups; and, (3) a step of measuring lengths of the DNA fragments which belong to said groups, or length of the DNA probe extended by said complementary strand extension reaction; wherein the thus measured lengths obtained for every sequence of the bases of the DNA fragments around the 3' termini thereof are employed as fingerprints.

28 Claims, 4 Drawing Sheets

METHOD OF ANALYSIS OR ASSAY FOR POLYNUCLEOTIDES AND ANALYZER OR INSTRUMENT FOR POLYNUCLEOTIDES

BACKGROUND OF THE INVENTION (1) Field of the Invention

The present invention relates to diagnosis using DNA and an assay for properties of DNA as well as a method for DNA analysis or assay.

(2) Description of the Related Art

It has been becoming popular to use DNA for diagnosis of disease. In such diagnosis of disease, (1) a DNA probe having a complementary sequence to a target DNA is prepared and a probe assay is carried out to see if this DNA probe hybridizes with the target DNA; (2) a certain region of sequence coding for a target DNA is chosen and subjected to polymerase chain reaction amplification using two DNA probes (primers), the resulting DNA fragment is read or its length is examined, and based on the DNA fragment information obtained, assay is performed; etc. The thus obtained results are utilized for diagnosis or the like. These methods are applicable to analysis or assay for a single kind of DNA, at most, a few kinds of DNAs but not appropriate for DNA assay of a vast number of DNA fragments or total evaluation of long DNA.

However, DNAs or genomes in vivo function while interacting with each other. It is, therefore, strongly desired to collectively assess chromosomes or all DNAs contained therein. For example, in a spotlighted cDNAs among the genome-project, it has been attempted to detect the kind and amount of cDNA complementary to mRNA thereby to collectively grasp an organism, paying attention to the mechanism of DNA functioning in the organism that, where DNA functions in an organism, DNA information is first transcribed onto mRNA and a protein is synthesized based on the information to function the organism. In this attempt, cDNAs are fished out of a vital sample and the respective cDNAs are sequenced to analyze the frequency of each CDNA appearing in one tissue (body mapping).

The body mapping involves the following procedures. First, cDNA is prepared from mRNA (in a mixture of diverse cDNAs) and then cloned. *E. coli* containing cDNAs is spread and cultured on an agarose plate to obtain colonies, each of which contains one of the desired cDNAs. The desired cDNA is taken out and sequenced to identify the kind of cDNA. In a similar manner, a desired cDNA is taken out of each colony and sequenced, whereby the same cDNA often appears. When attention is given to one particular cDNA present in one tissue, the larger the amount of this particular cDNA, the more likely the particular cDNA corresponds to the gene strongly expressed in the tissue and as the result, the higher the frequency of the gene appearance in the colony. Accordingly, there is proposed a method for determining the frequency of CDNA appearance which comprises performing cDNA sequencing in many colonies to see how many times a particular cDNA appears in the colonies (Katsuji, Murakawa et al., Genomics, 23, 379–389 (1994)).

On the other hand, another attempt for DNA diagnosis has also been proposed, paying attention to a genome (DNAs in all chromosomes) or the entire profile of a particular chromosome. A fingerprinting technique called gene scanning, which is also called Landmark genome scanning (LGS method), involves the steps of selectively digesting DNA with 8 base cutter restriction enzyme (which digests once per 48 to 64 kbs) such as Not I, etc., binding the digested fragments to a radioisotope tag or a nucleotide labeled with fluorophore, separating the fragments by electrophoresis, then cutting the DNA fragments in a gel with a 4 base cutter restriction enzyme (which digests once per 44 to 256 bases), and subjecting the DNA fragment on the upper end of a polyacrylamide slab gel to two-dimensional electrophoresis. The thus obtained pattern is utilized as a fingerprint, thereby to comprehend the entire profile of DNA. An attempt includes use of the pattern for diagnosis, noting that a DNA pattern in normal cells is different from that of abnormal cells suffered from cancer, etc.

However, a good technique is not found so far, since it should be examined in the foregoing methods in which particular site of long DNA there is abnormality.

It is important for early detection of diseases or understanding of DNA function in cells to examine a long and large DNA or clarify the entire profile of a sample containing diverse cDNAs. As stated above, however, any good technique sufficient for the purpose has not been developed yet. According to the techniques explained hereinabove, it is necessary to determine the base sequences of very many clones. Much labor and time required make it impossible to practically apply these techniques to various samples. Conventional DNA probing is only enough to examine, at best, several to several ten kinds of DNAs in one cycle of operation but not suitable for assaying cDNAs or DNA fragments of several hundreds to thousands in one cycle of operation. In addition, the cDNA analysis methods described above are not applicable to detection of long DNA where abnormality is located.

On the other hand, the gene scanning technique can meet the foregoing requirements but encounter problems that a huge amount of enzymes are consumed in the second digestion with a restriction enzyme and in the two dimensional electropherogram, the abscissa which is a scale for length of the DNA fragment occurred in the first digestion and the ordinate which gives some scale for length of the ultimate fragment are not always quantitative so that it is difficult to construct a database with these data.

SUMMARY OF THE INVENTION

An object of the present invention is to overcome the foregoing problems and provide a novel fingerprinting technique, namely, a DNA assay method, which is applicable to various samples and is suitable for assaying a large number of CDNAs or DNA fragments and assaying a long DNA.

The DNA analysis or assay method of the present invention have the following characteristic features. Firstly, DNA contained in a sample is cleaved with a restriction enzyme to produce DNA fragments having lengths inherent to the sample. An oligomer with a known sequence is connected to the produced DNA fragment at the 3' terminus thereof to form a priming region. A DNA probe which hybridizes with this priming region, recognition sequence and several bases adjacent to the recognition sequence is prepared. This DNA probe consists of a set of sixteen (16) DNA probes in which, e.g., the 3' terminal two bases are combinations of substantially all of the bases. These sixteen (16) DNA probes are hybridized with a sample DNA, independently, to perform a complementary strand synthesis. The synthesized strand is labeled with a fluorophore, etc. The complementary strand synthesis product is subjected to gel electrophoresis for every kind of the DNA probes used when initiating the complementary strand synthesis, and the length of each fragment is determined to obtain a fingerprint. The construction of the present invention is briefly described hereinbelow.

A. A first aspect of the method of analysis or assay for nucleotides according to the present invention comprises:

1) a step of digesting DNA with a restriction enzyme;

2) a step of discriminating a difference in sequences of the DNA fragments obtained in step 1) above around the 3' termini thereof with the 3' terminal sequence of the labeled DNA probe (the labeled nucleotide incorporated upon the complementary strand synthesis may also be employed as a labeled DNA strand) and extending the labeled DNA probe by a complementary strand synthesis only when the terminal sequence matches to fractionate the DNA fragments into groups; and, 3) a step of measuring lengths of the DNA fragments which belong to said groups, or length of the labeled DNA probe extended by said complementary strand extension reaction;

wherein the thus measured lengths obtained for every kind of the base sequences of the DNA fragments around the 3' termini thereof are employed as fingerprints.

B. A second aspect of the method of analysis or assay for nucleotides according to the present invention comprises, at least:

1) a step of digesting DNA with a restriction enzyme;

2) a step of ligating a deoxynucleotide or an oligomer containing an analogue of the deoxynucleotide with the DNA fragments obtained in step 1) above at the 3' termini thereof;

3) a step of performing a complementary strand synthesis using a set of four (4) or sixteen (16) labeled DNA probes having arbitrary sequences complementary to the oligonucleotide connected above or to a part of the recognition sequence of one or two bases at the 3' termini thereof and having different terminal sequences, thereby to extend said labeled DNA probes; and, 4) a step of subjecting the strand extended by the complementary strand synthesis to gel electrophoresis to detect the DNA fragments.

In the methods A and B described above, the characteristic features of the present invention lie at least in that the label is biotin, a chemiluminescence reagent or a fluorophore; the DNA probes or the DNA fragments are detected by detecting a fluorophore; and the labeled DNA probes contain a set of sixteen (16) labeled DNA probes wherein at least two terminal bases are composed of substantially all of the bases species or analogues thereof.

C. A third aspect of the method of analysis or assay for nucleotides according to the present invention comprises, at least:

1) a step of digesting DNA with a restriction enzyme;

2) a step of ligating a deoxynucleotide or an oligomer containing an analogue of the deoxynucleotide with the DNA fragments obtained in step 1) above at the 3' termini thereof;

3) a step of performing a complementary strand synthesis using each of the labeled DNA probes having all combinations of 1 to 3 bases consisting of arbitrary base species at the 3' termini thereof, which are complementary to the oligonucleotide connected at the step 2) above or to a part of the recognition sequence recognized by said restriction enzyme, thereby to extend the complementary strand of each of said labeled DNA probes;

4) a step of classifying and separating the DNA strand extended by the complementary strand synthesis for each of the labeled DNA probes in terms of terminal sequence;

5) a step of introducing a second oligomer into the DNA strand extended by the complementary strand synthesis at the 3' terminus thereof;

6) a step of performing the steps 3) and 4) using the DNA strand having the second oligomer introduced thereinto as a template; and, 7) a step of fractionating and detecting the DNA strands extended by the complementary strand synthesis, depending upon length.

In the method C described above, the characteristic feature of the present invention lies in that by the step of repeating the steps 3) and 4) described above, the DNA fragments or the complementary strands of the DNA fragments can be fractionated from each other, for each of the terminal base sequence of the labeled second DNA probe having a complementary strand to the second oligomer, thereby to detect the DNA. By repeating the steps 3) and 4) described above, the number of fractions can be increased so that more detailed analysis can be done. Furthermore, the method C is applicable to a sample containing much more fragments.

D. A fourth aspect of the method of analysis or assay for nucleotides according to the present invention comprises, at least:

1) a step of digesting DNA with a restriction enzyme;

2) a step of ligating a deoxynucleotide or an oligomer containing an analogue of the deoxynucleotide with the DNA fragments obtained in step 1) above at the 3' termini thereof;

3) a step of performing a complementary strand synthesis using a first labeled DNA probe having all combinations of 1 to 3 bases consisting of arbitrary base species at the 3' termini thereof, which are complementary to the oligonucleotide (or oligomer) connected at the step 2) above or to a part of the recognition sequence recognized by said restriction enzyme, thereby to extend the complementary strand of the first labeled DNA probe;

4) a step of classifying and separating the DNA strand complementary to the DNA strand extended by the complementary strand synthesis, for each of the terminal bases of the first labeled DNA probe;

5) a step of again performing the step 3) described above, using a second labeled DNA probe different from the first labeled DNA probe used in the step 3) above; and,

6) a step of fractionating and detecting the DNA strands extended by the complementary strand synthesis, which was produced from the second labeled DNA probe obtained in the step 5) above, depending upon length.

In the methods A through D described above, the characteristic feature of the present invention resides in that said restriction enzyme is a restriction enzyme to form a 3'-protruding end or blunt end type fragment. The characteristic features of the present invention in the methods A to D further reside in that the restriction enzyme used therein is a restriction enzyme to give a 5'-protruding end and the methods further include, after the step 1) described above, a step of filling the digested portions with the restriction enzyme using a DNA polymerase to form a double strand, or a step of introducing an oligomer containing the sequence of the digested portions by ligation.

In the method A, the characteristic feature of the present invention lies in that the complementary strands to the DNA fragments fractionated based on a difference in two bases is labeled, at least, with a fluorophore or a chemiluminescence reagent and produced by complementary strand synthesis, using labeled DNA probes having all possible combinations of arbitrary two bases at the 3' termini thereof.

E. The labeled DNA probes used in the methods A to D are a set of at least sixteen (16) DNA probes in all combinations of $N_1, \ldots, N_n$ (wherein $5 \leq n \leq 27$), $X_1, \ldots, X_m$ ($1 \leq m \leq 6$); $Y_1 Y_2$ is any one of A, C, G and T; said labeled DNA probes, which are primers used for the complementary strand synthesis, are represented by:

$$5'-N_1 \ldots N_n, X_1 \ldots X_m Y_1 Y_2-3'$$

wherein $N_1 \ldots N_n$ has a substantially complementary sequence to the oligomer connected to the DNA fragment; $X_1 \ldots X_m$ is substantially complementary to a part of the sequence of the portion digested with the restriction enzyme; and $Y_1 Y_2$ is composed of any combination of two out of A, C, G and T.

F. In the methods A to D, the labeled DNA probes employed are a set of at least sixteen (16) DNA probes in all combinations of $N_1, \ldots, N_n$ (wherein $5 \leq n \leq 27$) $X_1, \ldots, X_m$ ($1 \leq m \leq 6$); $Y_1 Y_2$ is any one of A, C, G and T; $Z_i$ ($1 \leq i \leq 3$) is a nucleotide analogue which can hybridize with a plural kinds of nucleotides; said labeled DNA probe which is a primer used for the complementary strand synthesis, is represented by:

$$5'-N_1 \ldots N_n X_1 \ldots X_m Z_i \ldots Z_i Y_1 Y_2-3'$$

wherein $N_1 \ldots N_n$ has a substantially complementary sequence to the oligomer connected to the DNA fragment; $X_1 \ldots X_m$ is substantially complementary to a part of the sequence of the portion digested with the restriction enzyme; and $Y_1 Y_2$ is composed of any combination of two out of A, C, G and T.

In the DNA probes of F, the present invention is characterized in that any one of the nucleotides of $N_1, \ldots, N_n$ is labeled, at least, with biotin or a fluorophore.

G. In the methods A to D, the DNA digested with a restriction enzyme is the DNA obtained by 1) a step of collecting mRNA from a tissue sample to prepare a mRNA-cDNA complementary pair, and 2) a step of preparing a double stranded DNA from the mRNA-cDNA complementary pair, thereby to give information on the kind and amount of mRNA.

H. A further aspect of the present invention relates to a DNA analyzer or instrument for DNA assay comprising:
a first reaction vessel for digesting DNA with a restriction enzyme;
a plurality of second reaction vessels for performing a second reaction which comprises:
mixing any one of a plurality of labeled DNA probes having different base sequences around the 3' termini thereof in each of a plurality of the second reaction vessels, in which the digestion products are fractionated and charged;
discriminating a difference in the base sequences of DNA fragments around the 3' termini thereof, which were obtained by the digestion above, with the labeled DNA probes;
extending the labeled DNA probe by a complementary strand synthesis only when the terminal sequence matches to fractionate the DNA fragments into groups; and,
a device for electrophoresis for measuring lengths of the DNA fragments belonging to the groups or, using the labeled DNA probe extended by the complementary strand synthesis as samples and measuring lengths of the samples;
thereby to obtain the length of the measured sample for each of the base sequences of the DNA fragments around the 3' termini thereof as a fingerprint.

I. A still further aspect of the present invention relates to a DNA analyzer or assay for nucleotides comprising:
a first reaction vessel for digesting DNA with a restriction enzyme and ligating a deoxynucleotide or an oligomer containing an analogue of the deoxynucleotide with the DNA fragments obtained in the digestion above at the 3' termini thereof;
a plurality of second reaction vessels for performing a second reaction which comprises:
mixing any one of a set of four (4) or sixteen (16) labeled DNA probes having arbitrary sequences complementary to the oligonucleotide connected above or to a part of the recognition sequence of one or two bases at the 3' termini thereof and having different terminal sequences, in each of a plurality of the second reaction vessels, in which the digestion products are fractionated and charged;
and,
a device for electrophoresis for measuring lengths of the DNA strands extended by the complementary strand synthesis using the thus extended DNA strands as samples;
whereby a length of the resulting sample given for each of the labeled DNA probes is obtained as a fingerprint.

In the DNA analyzers or assay instruments H and I, the present invention is characterized in that length markers are electrophoresed in a gel electrophoretic passway in the device for electrophoresis, together with the samples thereby to fractionate and discriminate the sample fragments separated by the electrophoresis and the samples and the length markers are tagged with fluorophore and hence, discriminated by a fluorescent wavelength of the fluorophore tag.

J. A still further aspect of the present invention relates to a DNA analyzer or assay for nucleotides, wherein a plurality of the reaction vessels and a chemical reaction vessel for performing a chemical reaction while controlling temperature are provided and a set of at least sixteen (16) labeled DNA probes are separately charged in a plurality of the reaction vessels, respectively, and each of the DNA fragments charged respectively in a plurality of the reaction vessels is simultaneously reacted with the labeled DNA probe.

Even though many DNA fragments to be analyzed are present in a sample, each DNA fragment has a different sequence from that adjacent to a recognition sequence in most cases. Therefore, DNA fragments are initially fractionated into groups depending upon the difference in sequence adjacent to the recognition sequence. This grouping operation is repeated until the number of DNA fragments in each group is reduced to such a level that does not cause any inconvenience for fractionation of the DNA fragments by gel electrophoresis. Finally, the DNA fragments in each group are determined by gel electrophoresis with a length of each DNA fragment.

The DNA fragments in a sample which are obtained by digesting DNA with a restriction enzyme are fractionated and classified by complementary strand synthesis, using a set of sixteen (16) DNA probes having the two terminal bases in all combinations. The complementary strand synthesis proceeds when the two terminal bases fully hybridize with the target DNA but if not, does not proceed. The DNA strand extended by the complementary strand synthesis has substantially the same length as that of the intact DNA strand (DNA fragment obtained by digestion with a restriction enzyme). When it is so designed that a label is taken up into the DNA strand extended by the complementary strand synthesis to make the labeled DNA strand is detectable distinguishably from other DNA strands extended by complementary strand synthesis, the terminal two bases are discriminated to determine the length of the intact DNA strand.

Where a single fractionation is insufficient for discriminating the DNA fragments obtained by digesting DNA in a sample with a restriction enzyme, biotin is tagged to DNA probe and the extended strand alone is fished out. Again the same fractionation is applied to the fished DNA fragment (extended DNA strand by complementary strand synthesis). In this case, a DNA probe employed is the one attached to the complementary strand at the 3' terminus (which corresponds to the 5' terminus of intact DNA) so that different classification from the first operation may be carried out.

That is, according to the present invention, information on lengths of many DNA fragments obtained by digesting DNA in a sample with a restriction enzyme is not utilized as fingerprints. Instead, the DNA fragments obtained by digestion with a restriction enzyme are fractionated by the terminal base sequence and classified into groups. With respect to the DNA fragment present in each group, the fragment length is measured by gel electrophoresis and used as a fingerprint. Accordingly, the present invention is advantageous in that the fragment length does not overlap with each other but a high resolution is obtained.

The present invention is applicable to various samples without much labor and time and can provide the fingerprinting method suitable for assay of many DNA or DNA fragments or analysis or assay for long DNA, as well as the analyzer or instrument in use therefor.

According to the present invention, steps of cloning and culture, which were necessary for display of mRNA for gene expression analysis in the prior art and required a long period of time, are unnecessary so that display of mRNA can be made in a shorter time which is less than one-tenth of the prior art. In addition, the data thus obtained can be converted into digital data which are preferable database for handling.

Figure 1:
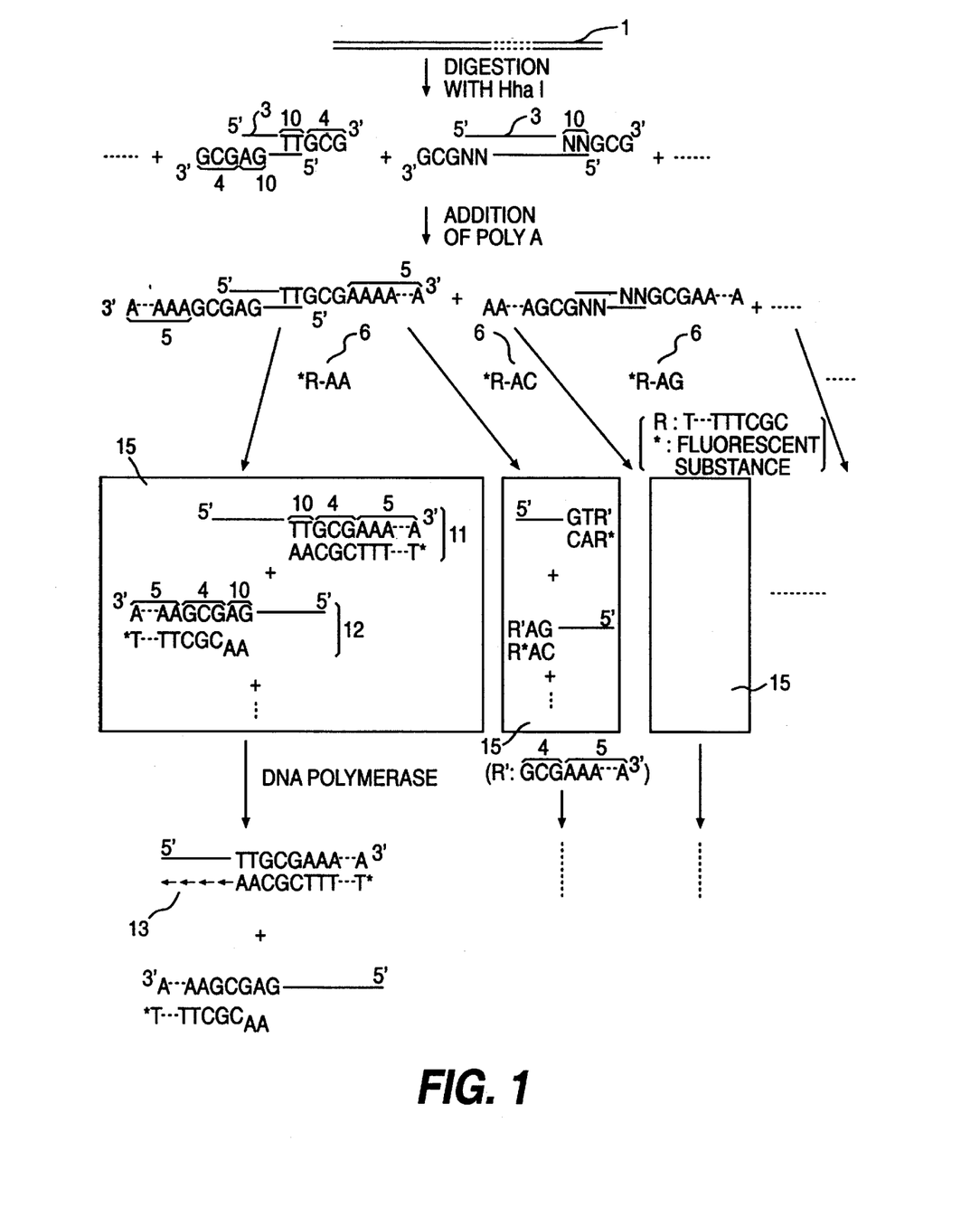
FIG. 1 is a drawing for explaining the operational procedures in Example 1 of the present invention.

Hereinafter the present invention will be described by referring to FIG. 1. Sample 1 is digested with restriction enzyme HhaI and poly A is added to the 3' terminal base sequence four (4) of each DNA fragment. A set of sixteen (16) fluorophore tagged DNA probes 6 having a structure of RXY (wherein X and Y represent A, C, G or T) are prepared. A solution containing sample DNA composed of all of the fragments is divided into sixteen (16) fractions 15 and different DNA probes 6 are added to the respective fractions to perform complementary strand synthesis. The DNA probe hybridizes with the DNA fragment but only the DNA probe (*R-AA) which fully hybridized at the 3' terminus as in 11 is extended by complementary strand synthesis. A complementary strand 13 having the same length of the extended DNA sequence, the length of the extended complementary strand is appreciated using a fluorescent gel electrophoresis device. In gel electropherogram, the fragment length does not overlap with each other but a high resolution in length is obtained. The method and analyzer or instrument are thus applicable to various samples.

DESCRIPTION OF THE PREFERRED EMBODIMENTS

The present invention is applicable to polynucleotide samples such as DNA or RNA. Analysis or assay for polynucleotide samples are performed by a fingerprinting analysis or an assay using fingerprinting method. The present invention further relates to a DNA analyzer or an instrument for DNA assay in use for the DNA analysis or DNA assay.

The embodiments of the present invention will be described below in detail, with reference to the drawings.

EXAMPLE 1

In Example 1, the present invention is explained, focusing on its basic principle. For DNA diagnosis, there has been generally employed a technique for digesting DNA with a restriction enzyme, fractionating the resulting DNA fragments by gel electrophoresis and perform diagnosis based on the electropherogram obtained. However, where the kind of DNA fragments produced by a restriction enzyme increases, the DNA fragments are not discriminated from each other to cause a problem in diagnosis. These fragments are characterized by the base lengths and sequences. Though each fragment has a sequence inherent thereto, the terminal sequences each consisting of several bases are also generally different from each other. For example, the digestion site by a 4-base cutter restriction enzyme generally appears at every 256 bp in average. Thus, when a double stranded DNA of approximately 50 kb is digested with a 4-base cutter restriction enzyme, about 200 double stranded DNA fragments (about 400 single stranded DNA fragments) are formed. These DNA fragments are first fractionated by the 3' terminal sequence of two bases adjacent to the recognition sequence, the number of combinations of the two base sequence becomes 4×4=sixteen (16) combinations. An average number of single stranded DNA fragments belonging to each group is approximately 25 fragments. It is easy to fractionate approximately 25 DNAs having various lengths from several bases to 1 kbs. Where intact DNA is long or where a sample containing many more DNA fragments is handled, the DNA fragments are grouped using a longer base sequence. For example, where grouping is performed by the terminal 4 base sequence, the DNA fragments are fractionated into 256 groups. When the DNA fragments in each group are fractionated by length, at least 100 kinds of DNA fragments having several bases to 1000 bases can be discriminated so that more than 20,000 DNA fragments can be fractionated as a whole. The thus obtained data can be employed as fingerprints. Next, specific procedures are explained below in detail, by referring to FIG. 1.

λDNA is used as sample 1 and as a restriction enzyme HhaI is used. HhaI is a restriction enzyme which digests double stranded DNA:

```
5'-N ... NGCGCN ... N-3'
3'-N ... NCGCGN ... N-5'
``` as shown below:

```
5'-N ... NGCG          CN ... N-3'
3'-N ... NC            GCGN ... N-5'
``` wherein N represents any one of A, T, G and C. The 3' terminal base sequence 4 of each DNA fragment 3 is GCG. in FIG. 1, two bases 10 adjacent to the 3' terminal base sequence 4 of each DNA fragment 3 is generally shown by NN, wherein N is any one of A, C, G and T.

An oligomer is introduced into the DNA fragment 3 at the 3' terminus thereof through ligation. Alternatively, poly A (which may be one base of A, C, G and T) is added to the DNA fragment at the 3' terminus thereof using a terminal deoxynucleotidyl transferase. Where poly A is added, the 3' terminus should be either 3'-protruding end or blunt end. By referring to FIG. 1, an embodiment in which poly A 5 is added is explained. When poly A 5 is added to each DNA fragment at the 3' terminus thereof, the 3' terminal sequence is represented by:

```
GCGAAAA ... A-3'
```

Where poly A is added, the presence of recognition sequence GCG is critical for clarifying the terminal site. This is because the length of poly A cannot be controlled. Therefore, a set of sixteen (16) DNA probes 6 having a construction shown by SEQ NO. 1:

```
5'-TTTTTTTTTTTTTTTTTTTCGCXY-3'
``` wherein X and Y each represents A, C, G or T, are prepared (the sixteen (16) DNA probes are all possible combinations of X and Y). In FIG. 1, these DNA probes are shown by: RXY, wherein X and Y each represents A, C, G or T and R represents TTTTTTTTTTTTTTTTTTTCGC. In FIG. 1, symbol * represents a fluorophore tag. Where the sequence CGC is missing, XY portion may not function for the discrimination of DNA fragments with respect to TG, TC, TT, TA, etc. (this is because XY is linked with poly T).

The sequence from the 5' end to CGC of the DNA probes is complementary to all of the DNA fragments obtained by digestion with restriction enzyme HhaI and hybridizes commonly with all of these fragments. An embodiment wherein XY (i.e., two bases 10 adjacent to the 3' terminal base sequence 4) is AA, is explained below. In this case, the XY portion hybridizes only with a fragment having complementary strand sequence TT to form double strand 11. Where the XY portion 10 has no complementary sequence to the fragment, the XY portion does not hybridize with any fragment, which is shown by numeral 12. It is not apparently appreciated only by stability of hybridization whether or not the portion XY fully hybridized. This is because almost all sites of the DNA probes hybridize commonly with any fragment but a difference in the terminal two base sequence is not sufficient for the discrimination.

However, by a complementary strand synthesis using a DNA polymerase, it can be discriminated whether or not the terminal two bases fully hybridize. A solution containing sample DNA composed of all DNA fragments obtained by digestion with restriction enzyme HhaI is divided into sixteen (16) fractions 15. Each different DNA probe 6 is added to each fraction for complementary strand synthesis. The DNA probes hybridize with the DNA fragments but only the DNA probe (*R-AA), in which the 3' end fully hybridizes, as shown by numeral 11, is extended by complementary strand extension, thereby to obtain complementary strand 13 having the same length as that of the DNA fragment. Where the DNA probes are labeled with a fluorophore, the length of the extended complementary strand can be appreciated using a device for fluorescence gel electrophoresis.

Figure 2A:
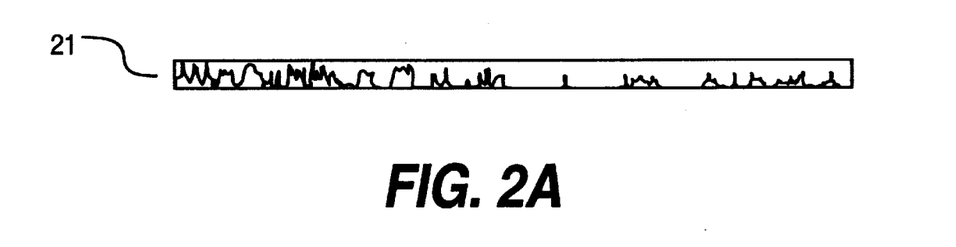
FIG. 2A shows an electropherogram measured by mixed DNA fragments obtained by applying the operational procedures in Example 1 of the present invention to sample -DNA.
Figure 2B:
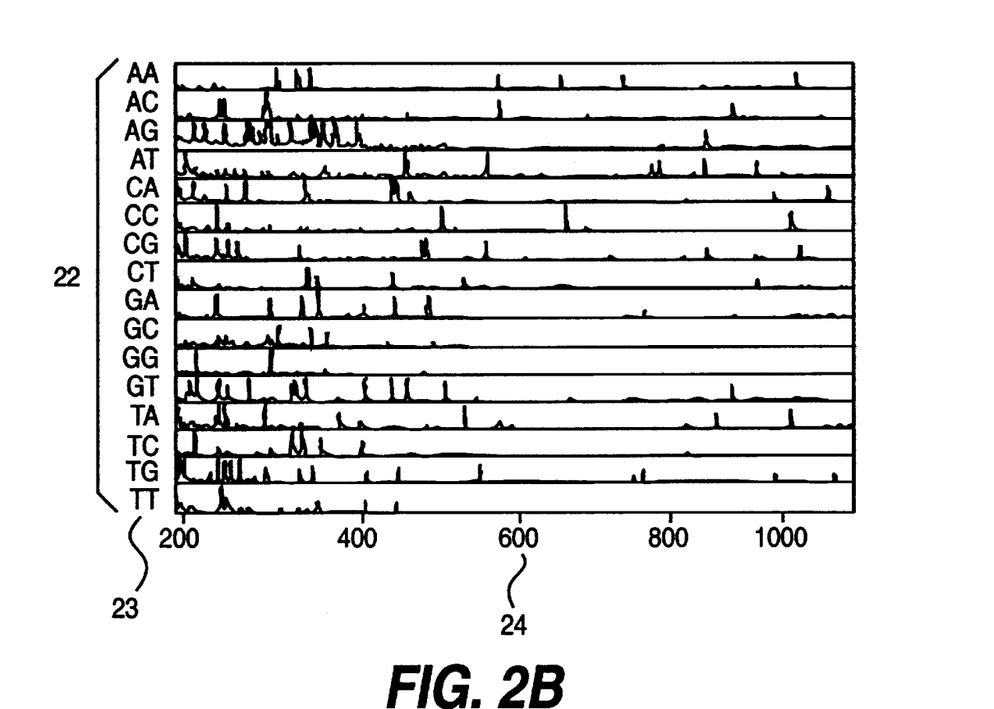
FIG. 2B shows an electropherogram measured by classified DNA fragments in terms of the terminal base sequences, which are obtained by applying the operational procedures in Example 1 of the present invention to sample -DNA, using a set of sixteen (16) DNA probes.

FIGS. 2A and 2B indicate a part of the results obtained using -DNA. Where it is attempted to simultaneously measure lengths of all DNA fragments obtained by digestion with restriction enzyme HhaI, many peaks overlap with each other as shown by electropherogram 21 in FIG. 2A, which makes discrimination impossible. However, in electropherogram 22 of the DNA fragments grouped by the terminal base sequence, using a set of sixteen (16) DNA probes 23 (in FIG. 2B, only the XY portion of the DNA probe *RXY is shown) the respective peaks corresponding to the respective fragments are separated from each other as shown in FIG. 2B. Accordingly, a length of each DNA fragment in the grouped DNA fragments can be determined. The electropherogram of each DNA fragment shown in FIG. 2B is inherent depending upon kind of intact DNA to be analyzed; if the structure of intact DNA is different, another electropherogram appears. Thus, these electropherograms can be utilized as fingerprints, which are in turn utilized for DNA diagnosis, etc. In FIGS. 2A and 2B, the abscissa indicates base length 24.

EXAMPLE 2

Figure 3A:
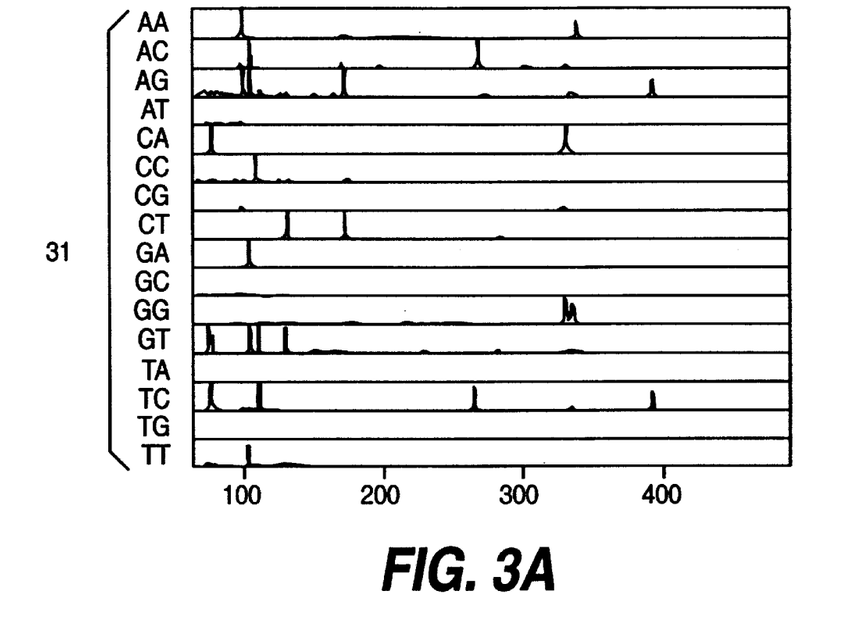
FIG. 3A shows an electropherogram from pUC19, which is obtained in Example 2 of the present invention.
Figure 3B:
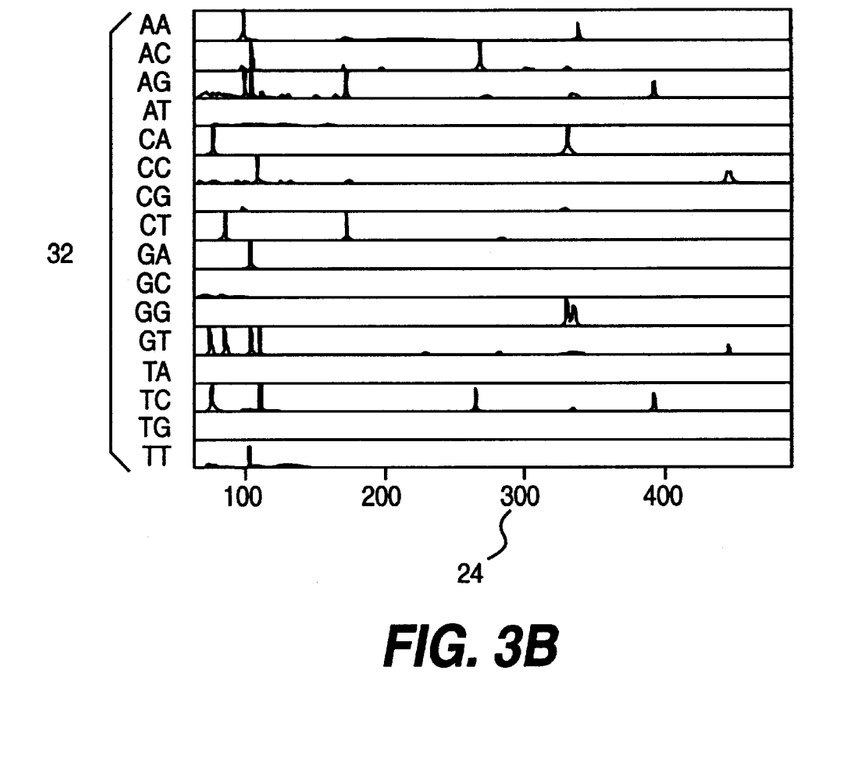
FIG. 3B shows an electropherogram from pUC118, which is obtained in Example 2 of the present invention.

FIGS. 3A and 3B indicate the results obtained by applying the present invention to the discrimination of different DNAS. The operational procedures are similar to Example 1. Two kinds of pUC having somewhat different base sequences are employed as samples, which are pUC19 and pUC118. pUC19 and pUC118 are DNA composed of 2686 bases and DNA composed of 3162, respectively, in which approximately 2630 bases give the same common sequence. After digestion with restriction enzyme HhaI, an oligomer with a known sequence at the terminus of the digested fragment is added by ligation. Thereafter in a manner similar to Example 1, the DNA fragments are grouped by the terminal base sequence of the digested fragment using a set of sixteen primers (DNA probes) and the electropherogram of each group is obtained.

The electropherograms 31 shown in FIG. 3A are those from pUC19. The electropherograms 32 shown in FIG. 3B are those from pUC118. The abscissa in FIGS. 3A and 3B represents base length 24. As the fragments which are missing in the electropherograms from pUC19 but detected only in the electropherograms from pUC118, about 75 bases (CT, GT primers) and about 450 bases (CC, GT primers) are noted and as the fragment detected only in pUC19, about 130 bases (CT, GT primers) are found.

As stated above, by applying the method of the present invention, various DNAs which are slightly different from each other can be discriminated in a simple manner. Of course, the present invention is also applicable to genomic DNA. When DNA is digested with restriction enzyme HhaI, the digestion site is found once per 250 bases in average, since HhaI is a 4-base cutter restriction enzyme. In the case of genome, about 100 double stranded DNA fragments in average are produced per 1M base. Where a 8-base cutter restriction enzyme such as NotI, etc., is employed in assaying a genome of about 100M bases, DNA fragments of almost the same order are produced and hence, the method described hereinabove is applicable to this case as it stands.

It is extremely difficult to fractionate such a vast number of DNA fragments (2000 to 3000 fragments when calculated as single strands) by gel electrophoresis and fine a slight difference in their electropherograms. Therefore, DNA fragments are classified into 16 groups in terms of the 3' terminal sequence of each DNA fragment digested with a restriction enzyme, whereby approximately 150 DNA fragments in average are contained in one group. Since this number is smaller than the number shown in Example 1, the DNA fragments can be analyzed in a manner similar to Example 1.

Complementary strand synthesis is greatly affected by whether or not the 3' terminal two bases are fully complementary to the target DNA (DNA fragment) of the DNA probes. This phenomenon is utilized to divide the formed DNA fragments into 16 groups. The DNA fragments are represented by:

wherein $X_n \ldots X_l$ is a sequence inherent to each fragment; $C_i \ldots C_1$ and $C'_1 \ldots C'_i$ represent recognition sequences or a part thereof and are known. 18-mer oligomers, $A'_1 \ldots A'_{18}$, $A_{18} \ldots A_1$, are ligated with this DNA fragment at the 5' and 3' termini thereof, respectively. As the result, each DNA fragment comes to have the following structure:

$A_{18} \ldots A_1$ and $A'_1 \ldots A'_{18}$ are oligomer with known sequences. In each DNA fragment, the sequence of $C_iC_1A_{18} \ldots A_1$ is known and several bases in the 3' terminal $X_n \ldots X_1$ adjacent to the known sequence are utilized for grouping of the DNA fragments.

DNA probes which hybridize with this DNA fragment are prepared. Such DNA probes are those complementary to $A_1 \ldots A_{18}C_1 \ldots C_i$ of the DNA fragment and fully hybridize with the specific sequence of $X_1X_2$. Since $X_1X_2$ takes 16 possible combinations, sixteen (16) DNA probes are prepared. The DNA probes are represented by:

A DNA analogue such as inosine may be inserted between $C'_i$ and $Y_1$ or in place of $C'_i$ and the resulting probe may also be employed. This DNA probe is tagged with biotin (B); if necessary and desired, the tagged probe is designed to be isolated by a microtiter plate having streptavidin immobilized thereto or by magnetic beads, etc. In the above explanation, $C_1, \ldots, C_i; C'_1, \ldots, C'_i; X_i \ldots, X_n; Y_1, Y_2; A_1 \ldots A_{18}; A'_1, \ldots, A'_{18}$ represent any one of A, C, G and T; and,
sequence $C_1 \ldots C_i$ and sequence $C'_1 \ldots C'_i$; sequence $A_1 \ldots A_{18}$ and sequence $A'_1 \ldots A'_{18}$; and sequence $X_1X_2$ and sequence $Y_1Y_2$ form complementary strands as will be later shown in FIG. 4.

Figure 4:
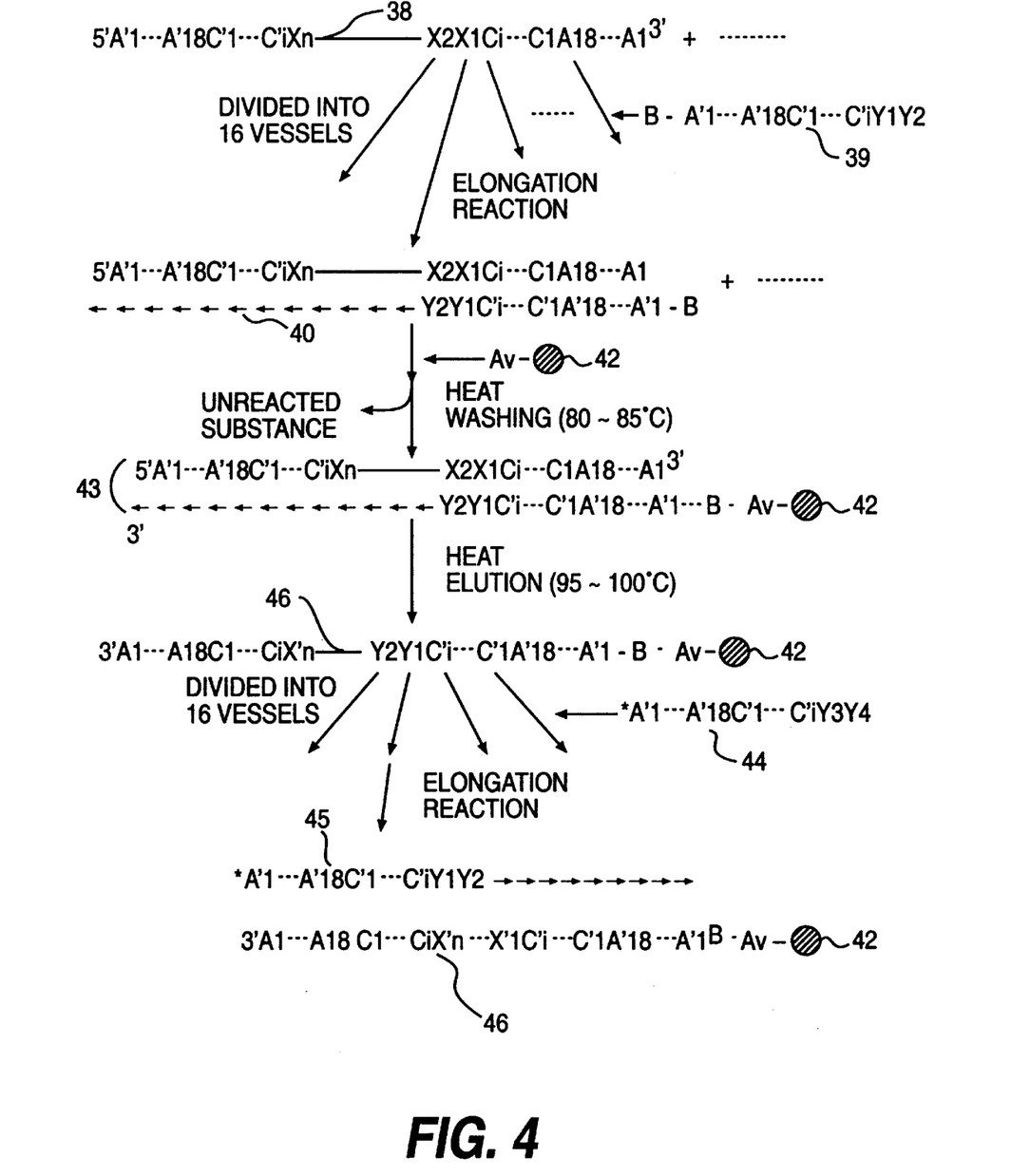
FIG. 4 is a drawing for explaining the operational procedures in Example 2 of the present invention.

The present invention will be further described in detail, by referring to FIG. 4. DNA sample 38 (18-mer oligomers with known sequences: $A'_1 \ldots A'_{18}$ and $A_{18} \ldots A_1$ are connected to each DNA fragment at the 5' and 3' termini thereof, respectively; which was obtained by digesting DNA with HindIII and the thus obtained DNA fragments were grouped) is divided into 16 fractions. Each fraction is separately charged in a vessel. One biotinylated DNA probe 39 (wherein B represents biotin):

is added to each fraction. DNA polymerase and substrates for strand synthesis (dNTP; deoxynucleotide triphosphate) are further added thereto to perform a complementary strand extension reaction.

As a DNA polymerase, thermostable Taq or thermostable sequenase is employed. The reaction is carried out under conditions of thermal cycling to synthesize a complementary strand of the DNA fragment completely complementary to the terminal sequence of DNA probe. After the complementary strand synthesis, magnetic beads 42 with streptavidin (Av) on its surface are added to capture the biotin-labeled synthesized DNA strand 40 on the beads. Plastic beads or filters having streptavidin immobilized thereto may also be employed in place of magnetic beads. The non-reacted substances captured other than the DNA strand are removed. As described above, sixteen (16) groups 43 are prepared for each DNA fragment having a specific terminal sequence:

In this Example, complementary strand to each DNA fragment is employed for the grouping. By elevating a temperature of the solution containing DNA fragments, intact DNA fragments hybridized are liberated and removed. As shown in FIG. 4, the group of complementary strands (DNA strand) 46 of recovered fragment have a common probing sequence at the 5' terminus (the DNA probe sequence is located at the 5' terminus of the synthesized strand after complementary strand synthesis) and are fractionated into 16 groups, by a difference in the two bases adjacent to the probing sequence. Each group contains 150 DNA strands in average.

The DNA fragments in each group are further discriminated and classified in terms of a difference in the 3' terminal sequence (the 3' terminal sequence corresponds to the 5' terminal sequence of intact DNA fragment used as a template in the complementary strand synthesis). The DNA strand 46 captured on the beads contains an oligomer sequence $A_1 \ldots A_{18}$ connected upon ligation, with which the DNA probe can hybridize. A set of sixteen (16) fluorophore tagged probes 44 having the same sequence as described above:

wherein * is a fluorophore tag and $Y_3$ and $Y_4$ represent any one of A, C, G and T. The DNA fragments captured on the beads are divided into 16 fractions.

As in the embodiment described above, one DNA probe is added to each fraction to perform a complementary strand synthesis (extension reaction). The reaction is carried out with 16×16=256 groups and the electropherogram of the extended product 45 is assayed. The aforesaid fluorophore tag may be altered for every probe, probes labeled with fluorophores having different colors are reacted at once, and the extended product 45 may be assayed with a multicolor detection type DNA analyzer. When using fluorophores with four different colors, it is sufficient to perform the reaction 4 times for each DNA group, i.e., 4×16=64 times in total. In addition, 64 passways are sufficient for electrophoresis. In this embodiment, the oligomer connected to the terminus was regarded as the same but different restriction enzymes may also be used at the both termini so that different sequences may be connected at the termini.

Comparison in electropherograms between E. coli JM109 and C600, which genomes are slightly different, reveals that most are the same but there is a difference in a part, like for example of pUC19 and pUC118 as shown in FIGS. 3A and 3B. The difference will not be notable when electrophoresed without grouping.

As stated above, after a large DNA is digested with a restriction enzyme, the DNA fragments are grouped by a sequence around the two termini and subjected to electrophoresis to obtain a pattern for length separation, whereby an electropherogram inherent to each genome can be obtained. The pattern is effective for examination of a difference in genome. In particular, the grouping by the terminal base species is effective also for constructing a database. In pattern data on two dimensional electrophoresis alone, DNA length given by analog information is uncertain so that it is difficult to construct a database. However, the grouping by the terminal base species in combination with digital information can accurately discriminate DNAS, even if the length separation by analog information is not highly accurate.

In the foregoing explanation, the temperature of the solution containing DNA fragments is elevated to isolate and remove the intact DNA fragment hybridized. The intact DNA fragment hybridized with the DNA probe extended by complementary strand synthesis may also be used after fractionation. In this case, the solution is first heated to 80°–85° C. to liberate and remove the DNA fragment hybridized with the probe not extended by complementary strand synthesis. The solution is then heated to 95°–100° C. thereby to liberate and recover the DNA fragment hybridized with the probe extended by complementary strand synthesis.

EXAMPLE 3

This embodiment is to obtain information relating to display of mRNA for gene expression analysis. The number of human genes is said to be 50,000 to 100,000 species. Accordingly, 50,000 to 100,000 species of mRNAs (messenger RNA) are present. Among these mRNAs, it is assumed that approximately 3,000 mRNAs would be regularly working. It is thus important to appreciate how these mRNAs function in various tissues. In order to examine the function of mRNAs, the existing technique comprises collecting mRNA, cloning mRNA, analyzing a sequence of mRNA present in each clone and detecting frequency of displaying mRNA. However, the procedures require much labor. It is thus desired to develop a simple operation for the analysis. Analysis of cDNA complementary to mRNA has been progressed, whereby it is also possible to prepare a DNA probe capable of specifically hybridizing with each cDNA and use the DNA probe for assay. However, probes practically usable are substantially limited to approximately several tens to 100 probes. Where cDNA that cannot be detected with a probe is detected, the use of limited probes is not practical. It is thus desired to develop a system which can detect any cDNA. In view of the existing situation, the present invention is applied to display of mRNA in this embodiment.

A mRNA library (cDNA library) is prepared from tissues (J. DNA Sequencing and Mapping, 2, 137–144 (1991). In accordance with the technique described in Nature, 357, 519–520 (1992), cDNA is prepared using biotinylated poly T, mRNA-cDNA hybrid is prepared and double stranded DNA is prepared. The double stranded DNA is digested with restriction enzyme Sau3AI and an oligomer with a known sequence is connected to the digested site. HhaI (GCG↓C) or NlaIII (CATG↓) may also be employed as the restriction enzyme.

By these procedures, a DNA fragment having biotinylated poly T sequence at the 5' terminus thereof and having a recognition sequence and known oligomer at the 3' terminus is formed. Magnetic beads having streptavidin immobilized thereon are added to the DNA fragment to form biotin-streptavidin complex. The complex captures the aforesaid DNA fragment and its complementary strand. A buffer solution is added to the beads having the DNA fragment immobilized thereto, which are charged in a vessel. The resulting mixture is heated to liberate the complementary DNA fragment. The complementary DNA fragment is used as a sample. Subsequently, the sample is treated as in Example 2 to fractionate DNA fragments in terms of the 3' terminal sequence adjacent to poly A of the DNA fragments. In this case, there are 12 selective sequences adjacent to poly T, unlike Example 2. After fractionation of biotinylated DNA probe, complementary strand synthesis is performed using sixteen (16) fluorophore tagged probes. A length of the produced DNA is measured by gel electrophoresis to obtain a fingerprint.

EXAMPLE 4

In order to carry out the method explained in Examples 1 to 3, a DNA analyzer comprises reaction vessels for reacting 16 or 256 DNA probes simultaneously to obtain the complementary strand extended products, an autopipet for automatically feeding each probe to each vessel, and a device for electrophoresis. It is preferred to carry out the complementary strand extension reaction at a temperature above 65° C., since it is apparently reflected by matching or mismatching the sequence of the terminal bases whether the reaction proceeds or not. It is also necessary to compare the relative length of the products by the complementary strand extension reaction by simultaneously subjecting the extended products to electrophoresis for every base of the terminal bases of DNA probe or by subjecting a length (reference) marker to electrophoresis at the same time, for each base of the terminal bases of DNA probe. For this reason, particularly preferred is such an instrument for determining a fragment length that a reference marker is electrophoresed together with each product by the complementary strand extension reaction and relative positional relationship between the fragment of the complementary strand extension reaction product fractionated by electrophoresis and the marker is utilized. In this case, operation is easily done by discriminating the length of DNA fragments by a plurality of markers having different lengths to arrange data in such a manner as to what group the DNA fragments belong. If DNA fragments up to 1 Kbs are fractionated into 200 groups by markers appearing for every 5 bases, the DNA fragments will be even fractionated into 256×200—50,000 groups. This number gives group sufficient for diagnosis of mRNA, etc. or for fingerprinting analysis.

Measurement accuracy in electrophoresis is high in base length ranging from 10 to 500 bases. Where DNA fragments are fractionated for every 2 bases, fractionated data can be obtained in more detail. In such measurement, it is desired to label the marker with a fluorophore having quite a different emission wavelength from that of a fluorophore for labeling the target DNA fragment so that the marker can be readily discriminated from the target DNA fragment. A fluorophore has a plain emission zone toward a longer wavelength direction. It is thus important for the marker not to interfere with desired measurement of DNA fragments, by selecting a kind of fluorophore used for the marker to tag the target DNA fragment and to have a fluorescent signal in a longer wavelength region. DNA fragments may have different structures depending upon sequence length and may have different mobilities in gel electrophoresis even when they have the same base length. Even in such a case, however, the DNA fragments can be fractionated if it is appreciated in which fraction DNA fragments are displayed, using a marker as a yardstick. That is, even though DNA fragments have the same length, the DNA fragment may be fractionated in different fractions due to a difference in sequence but good reproducibility of fractionation eliminates any problem upon analysis.

(2) introducing an oligomer comprising deoxynucleotides or an oligomer containing analogues of the deoxynucleotides into the DNA fragments at the 3' termini thereof, by using ligase or terminal deoxynucleotidyl transferase;

(3) performing a complementary strand synthesis using a first probe set comprising four labeled DNA probes or a second probe set comprising sixteen labeled DNA probes and complementary strand to the introduced oligomer or to a part of the recognition sequence recognized by the restriction enzyme thereby to extend said labeled DNA probes, wherein one base at 3' termini of the four labeled DNA probes of the first probe set is composed of all possible four combinations of one base species out of A, C, G and T or analogues thereof, and two bases at the 3' termini of the sixteen

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA, fluorophore tagged"

( x i ) SEQUENCE DESCRIPTION: SEQ ID NO:1:

T T T T T T T T T   T T T T T T T T C   G C N N                                                                                  2 4

What is claimed is:

1. A method of analysis or assay for nucleotides which comprises:
   (1) digesting DNA's with a restriction enzyme to obtain DNA fragments;
   (2) discriminating differences in sequences of two bases adjacent to restriction enzyme recognition sites of the DNA fragments with labeled DNA probes and extending the labeled DNA probes by a complementary strand synthesis to fractionate the DNA fragments into sixteen groups, wherein the labeled DNA probes have all possible sixteen combinations of two bases out of A, C, G and T at the 3' termini thereof; and
   (3) measuring lengths of the DNA fragments which belong to each of said sixteen groups, or lengths of the labeled DNA probes extended by said complementary strand synthesis;
   wherein measured lengths of the DNA fragments fractionated into the sixteen groups by the differences in sequences of two bases adjacent to the restriction enzyme recognition sites of the DNA fragments are employed as fingerprints.

2. A method of analysis or assay for nucleotides according to claim 1, wherein the complementary strands synthesized from the DNA probes are labeled with a fluorophore.

3. A method of analysis or assay for nucleotides which comprises:
   (1) digesting DNA with a restriction enzyme to obtain DNA fragments;

labeled DNA probes of the second probe set are composed of all possible sixteen combinations of two bases species out of A, C, G and T or analogues thereof; and (4) subjecting the strand extended by the complementary strand synthesis to electrophoresis to detect the DNA fragments and to obtain each of four electropherograms or each of sixteen electropherograms;

wherein the four electropherograms are classified by differences in sequences of one base adjacent to restriction enzyme recognition sites of the DNA fragments, and the four electropherograms are employed as fingerprints, or the sixteen electropherograms are classified by differences in sequences of two bases adjacent to the restriction enzyme recognition sites of the DNA fragments, and the sixteen electropherograms are employed as fingerprints.

4. A method of analysis or assay for nucleotides according to claim 1, wherein the label is any one selected from biotin and a chemiluminescence reagent.

5. A method of analysis or assay for nucleotides according to claim 1, wherein the label is a fluorophore and the DNA probes or the DNA fragments are detected by detecting a fluorophore.

6. A method of analysis or assay for nucleotides which comprises:
   (1) digesting DNA's with a restriction enzyme to obtain DNA fragments;
   (2) introducing a first and a second oligomer comprising deoxynucleotides or a first and a second oligomer containing analogues of the deoxynucleotides into the DNA fragments at the 3' and 5' termini thereof, respectively, by using ligase;

(3) performing a complementary strand synthesis using first labeled DNA probes having all possible combinations of 1 to 3 bases out of A, C, G and T or analogues thereof at the 31 termini thereof, the first labeled DNA probes being complementary to the introduced first oligomer or to a part of the recognition sequence recognized by said restriction enzyme, or using labeled nucleotide phosphate, thereby extending the complementary strand of each of said first labeled DNA probes;

(4) classifying and recovering the DNA strand extended by the complementary strand synthesis for each of the first labeled DNA probes;

(5) performing a complementary strand synthesis using second labeled DNA probes having all possible combinations of 1 to 3 bases out of A, C, G, and T or analogues thereof at the 3' termini thereof, the second labeled DNA probes being complementary to the DNA strand extended by the complementary strand synthesis in step (3) or to a part of the recognition sequence recognized by said restriction enzyme, or using labeled nucleotide phosphate, thereby extending the complementary strand of each of the second labeled DNA probes;

(6) fractionating and detecting the DNA strands extended by the complementary strand synthesis in step (5), depending upon length, for each of the second labeled DNA probes.

7. A method of analysis or assay for nucleotides according to claim 1, wherein said restriction enzyme is a restriction enzyme to form a 3'-protruding end.

8. A method of analysis or assay for nucleotides according to claim 1, wherein said restriction enzyme is a restriction enzyme to form a blunt end type fragment.

9. A method of analysis or assay for nucleotides according to claim 1, wherein said restriction enzyme is a restriction enzyme to give a 5'-protruding end and which further includes, after step (1), reassociating the digested portions with the restriction enzyme using a DNA polymerase to form a double strand.

10. A method of analysis or assay for nucleotides according to claim 1, wherein the complementary strands to the DNA fragments fractionated based on differences in sequences of two bases adjacent to the restriction enzyme recognition sites are labeled with a fluorophore or a chemiluminescence reagent and produced by complementary strand synthesis, using labeled DNA probes.

11. A method of analysis or assay for nucleotides which comprises:

(1) fractionating DNA fragments into sixteen groups by differences in sequences of two bases adjacent to a restriction enzyme recognition site of each of the DNA fragments obtained by digesting a sample DNA with a restriction enzvme, using labeled DNA probes having all possible sixteen combinations of two bases out of A, C, G and T at the 31 termini thereof; and (2) separating the DNA fragments contained in each of the sixteen groups or complementary strands to the DNA fragments by electrophoresis in terms of length;

wherein an electropherogram obtained by the electrophoresis is used for analysis or assay.

12. A method of analysis or assay for nucleotides according to claim 11, wherein the complementary strands to the DNA fragments fractionated based on differences in sequences of two bases adjacent to the restriction enzyme recognition site are labeled with a fluorophore or a chemiluminescence reagent and produced by complementary strand synthesis, using labeled DNA probes.

13. A method of analysis or assay for DNA which comprises:

(1) digesting DNA's with a restriction enzyme to obtain DNA fragments;

(2) discriminating differences in sequences of 1 to 3 bases adjacent to the restriction enzyme recognition sites of the DNA fragments with labeled DNA probes and extending the labeled DNA probes by a complementary strand synthesis to fractionate the DNA fragments into groups, wherein the labeled DNA probes have all possible combinations of 1 to 3 bases out of A, C, G and T at the 3' termini thereof; and (3) measuring lengths of the DNA fragments which belong to said groups, or lengths of the labeled DNA probes extended by said complementary strand synthesis;

wherein measured lengths of the DNA fragments fractionated into the groups by the differences in sequences of 1 to 3 bases adjacent to the restriction enzyme recognition sites of the DNA fragments termini are employed as fingerprints.

14. A set of sixteen DNA probes which are DNA probes used in a method of analysis or assay for nucleotides according to claim 1, and said labeled DNA probes are primers used for the complementary strand synthesis and represented by:

$$5'\text{-}N_1 \ldots N_n X_1 \ldots X_m Y_1Y_2\text{-}3'$$

wherein the sequence of $N_1, \ldots, N_n$ (wherein $5 \leq n \leq 27$) has a complementary sequence to the oligomer introduced to the DNA fragment; sequence of $X_1, \ldots, X_m$ ($1 \leq m \leq 6$) is complementary to a part of the sequence of the portion digested with the restriction enzyme; and sequences of $Y_1Y_2$ include all possible sixteen combinations of two bases out of A, C, G and T.

15. A set of sixteen DNA probes which are DNA probes used in a method of analysis or assay for nucleotides according to claim 1, and said labeled DNA probes are primers used for the complementary strand synthesis and represented by:

$$5'\text{-}N_1 \ldots N_nX_1 \ldots X_m Z_1 \ldots Z_iY_1Y_2\text{-}3'$$

wherein sequence of $N_1, \ldots, N_n$ (wherein $5 \leq n \leq 27$) has a complementary sequence to the oligomer introduced to the DNA fragment; sequence of $X_1, \ldots, X_m$ ($1 \leq m \leq 6$) is complementary to a part of the sequence of the portion digested with the restriction enzyme; sequence of $Z_1 \ldots Z_i$ ($1 \leq i \leq 3$) is a nucleotide analogue which can hybridize with a plurality of nucleotides; and sequences of $Y_1Y_2$ include all possible sixteen combinations of two bases out of A, C, G and T.

16. A set of DNA probes according to claim 14, wherein any one of the nucleotides $N_1, \ldots, N_n$ is labeled with biotin or a fluorophore.

17. A method of analysis or assay for nucleotides which comprises:

(1) collecting mRNA from a tissue sample to prepare a mRNA-cDNA complementary pair;

(2) preparing a double stranded DNA from the mRNA-cDNA complementary pair;

(3) digesting the double stranded DNA with a restriction enzyme to obtain DNA fragments;

(4) discriminating differences in sequences of two bases adjacent to the restriction enzyme recognition sites of the DNA fragments with labeled DNA probes and extending the labeled DNA probes by a complementary strand synthesis to fractionate the DNA fragments into sixteen groups, wherein the labeled DNA probes have all Possible sixteen combinations of two bases out of A, C, G and T at the 3' termini thereof; and (5) measuring lengths of the DNA fragments which belong to each of said sixteen groups, or lengths of the labeled DNA probes extended by said complementary strand synthesis;

wherein measured lengths of the DNA fragments fractionated into the sixteen groups by the differences in sequence of two bases adjacent to the restriction enzyme recognition sites of the DNA fragments are employed as fingerprints to give information on the kind and amount of said mRNA.

18. A method of analysis or assay for nucleotides which comprises:

(1) collecting mRNA from a tissue sample to prepare a mRNA-cDNA complementary pair;

(2) preparing a double stranded DNA from the mRNA-cDNA complementary pair;

(3) digesting the double stranded DNA with a restriction enzyme to obtain DNA fragments;

(4) introducing an oligomer comprising deoxynucleotides or an oligomer containing analogues of the deoxynucleotides into the DNA fragments at the 3' termini thereof;

(5) performing a complementary strand synthesis using a first probe set comprising four labeled DNA probes or a second probe set comprising sixteen labeled DNA probes complementary to the introduced oligomer or to a part of the recognition sequence recognized by the restriction enzyme thereby extending said labeled DNA probes, wherein one base at the 3' termini of the four labeled DNA probes of the first probe set is composed of all possible four combinations of one base species out of A, C, G and T or analogues thereof, and two bases at the 3' termini of the sixteen labeled DNA probes of the second probe set are composed of all possible sixteen combinations of two bases species out of A, C, G and T or analogues thereof; and (6) subjecting the strand extended by the complementary strand synthesis to electrophoresis to detect the DNA fragments; thereby giving information on the kind and amount of said mRNA.

19. A method of analysis or assay for nucleotides which comprises:

(1) collecting mRNA from a tissue sample to prepare a mRNA-cDNA complementary pair;

(2) preparing a double stranded DNA from the mRNA-cDNA complementary pair;

(3) digesting the double stranded DNA with a restriction enzyme to obtain DNA fragments;

(4) introducing a first and a second oligomer comprising deoxynucleotides or a first and a second oligomer containing analogues of the deoxynucleotides into the DNA fragments at the 3' and 5' termini thereof, respectively, by using ligase;

(5) performing a complementary strand synthesis using a first probe set comprising four labeled DNA probes or a second probe set comprising sixteen labeled DNA probes complementary to the introduced oligomer in step (4) or to a part of the recognition sequence recognized by the restriction enzyme, thereby extending said labeled DNA probes of the first or second probe set, wherein one base at the 3' termini of the four labeled DNA probes of the first probe set is composed of all possible four combinations of one base species out of A, C, G and T or analogues thereof, and two bases at the 3' termini of the sixteen labeled DNA probes of the second probe set are composed of all possible sixteen combinations of two bases species out of A, C, G and T or analogues thereof;

(6) classifying and recovering the DNA strand extended by the complementary strand synthesis, for each of the labeled DNA probes of the first or second probe set;

(7) performing a complementary strand synthesis using a third probe set comprising four labeled DNA probes or a fourth probe set comprising sixteen labeled DNA probes complementary to the DNA strand extended by the complementary strand synthesis in step (5) or to a part of the recognition sequence recognized by the restriction enzyme, thereby extending said labeled DNA Probes of the third or fourth probe set, wherein one base at the 3' termini of the four labeled DNA probes of the third probe set is composed of all possible four combinations of one base species out of A, C, G and T or analogues thereof, and two bases at the 3' termini of the sixteen labeled DNA probes of the fourth probe set are composed of all possible sixteen combinations of two bases species out of A, C, G and T or analogues thereof, and the third probe set is different from the first probe set and the fourth probe set is different from the second probe set; and (8) fractionating and detecting the DNA strands extended by the complementary strand synthesis in step (7), depending upon length;

thereby giving information on the kind and amount of said mRNA.

20. A method of analysis or assay for nucleotides which comprises:

(1) collecting mRNA from a tissue sample to prepare a mRNA-cDNA complementary pair;

(2) preparing a double stranded DNA from the mRNA-cDNA complementary pair;

(3) fractionating DNA fragments obtained by digesting the double stranded DNA with a restriction enzyme into groups by differences in sequences of two bases adjacent to the restriction enzyme recognition site of each of the DNA fragments, using labeled DNA probes having all possible sixteen combinations of two bases out of A, C, G and T at the 3' termini thereof; and (4) separating the DNA fragments contained in each of the sixteen groups or complementary strands to the DNA fragments by electrophoresis in terms of length;

thereby giving information on the kind and amount of said mRNA.

21. A method of analysis or assay for nucleotides which comprises:

(1) collecting mRNA from a tissue sample to prepare a mRNA-cDNA complementary pair;

(2) preparing a double stranded DNA from the mRNA-cDNA complementary pair;

(3) digesting the double stranded DNA with a restriction enzyme to obtain DNA fragments;

(4) discriminating differences in sequences of 1 to 3 bases adjacent to the restriction enzyme recognition sites of the DNA fragments with labeled DNA probes and extending the labeled DNA probes by a complementary strand synthesis to fractionate the DNA fragments into groups, wherein the labeled DNA probes have all possible combinations of 1 to 3 bases out of A, C, G and T at the 3' termini thereof; and (5) measuring lengths of the DNA fragments which belong to each of said groups, or lengths of the labeled DNA probes extended by said complementary synthesis reaction;

wherein based on measured lengths of the DNA fragments fractionated into the groups by the differences in sequences of 1 to 3 bases adjacent to restriction enzyme recognition sites of the DNA fragments, said mRNA is analyzed or assayed thereby giving information on the kind and amount of said mRNA.

22. A method of analysis or assay for nucleotides which comprises:

(1) digesting DNA's with a restriction enzyme to obtain DNA fragments;

(2) discriminating differences in sequences of two bases adjacent to restriction enzyme recognition sites of the DNA fragments with labeled DNA probes and extending the labeled DNA probes by a complementary strand synthesis to fractionate the DNA fragments into sixteen groups, wherein the labeled DNA probes have all possible sixteen combinations of two bases out of A, C, G and T at the 3' termini thereof; and (3) measuring lengths of the labeled DNA probes extended by said complementary strand synthesis for each group of sixteen groups individually by electrophoresis to obtain an electropherogram for each group of sixteen groups;

wherein measured lengths obtained from the sixteen electropherograms are employed as fingerprints.

23. A method of analysis or assay for nucleotides which comprises:

(1) digesting a sample DNA with a restriction enzyme to obtain DNA fragments;

(2) introducing an oligomer into the DNA fragments at the 3' termini thereof;

(3) dividing a solution containing the DNA fragments into sixteen fractions;

(4) adding a different kind of labeled DNA probe to each of the sixteen fractions, respectively, and extending the labeled DNA probes by a complementary strand synthesis, wherein the labeled DNA probes have all possible sixteen combinations of two bases out of A, C, G and T at the 3' termini thereof; and (5) obtaining sixteen electropherograms by electrophoresis of the labeled DNA probes extended by said complementary strand synthesis in each of the sixteen fractions;

wherein each of the sixteen electropherograms is classified by differences in sequences of two bases adjacent to the restriction enzyme recognition sites of the DNA fragments, and the sixteen electropherograms are employed as fingerprints.

24. A method of analysis or assay for nucleotides which comprises:

(1) digesting a sample DNA with a restriction enzyme to obtain DNA fragments;

(2) introducing a first and a second oligomer having known sequences into the DNA fragments at the 3' and 5' termini thereof, respectively;

(3) dividing a solution containing the DNA fragments into sixteen first vessels;

(4) performing a complementary strand synthesis in each of the sixteen first vessels, respectively, using a different kind of first labeled DNA probes having all possible sixteen combinations of two bases out of A, C, G and T at the 3' termini thereof, the first labeled DNA probes being complementary to the introduced oligomer or to a part of the recognition sequence recognized by said restriction enzyme, thereby extending the complementary strand of the first labeled DNA probes;

(5) removing non-reacted substances in the solutions in each of the sixteen first vessels of step (4), respectively, and, by elevating the temperature of the solution, liberating the DNA fragments from the hybrids of the complementary strand synthesis and recovering the DNA strand extended by the complementary strand synthesis in step (4) in each of the sixteen first vessels;

(6) dividing a solution containing the recovered DNA strand extended by the complementary strand synthesis from each of the sixteen first vessels into sixteen second vessels;

(7) performing a complementary strand synthesis in each of the sixteen second vessels, respectively, using a different kind of second labeled DNA probes different from the first labeled DNA probes, the second labeled DNA probes having all possible sixteen combinations of two bases out of A, C, G and T at the 3' termini thereof, the second labeled DNA probes being complementary to the introduced oligomer or to a part of the recognition sequence recognized by said restriction enzyme, thereby extending the complementary strand of the second labeled DNA probes; and (8) obtaining 256 electropherograms by electrophoresis of the second labeled DNA probes extended by said complementary strand synthesis in each of the 256 vessels;

wherein each of the 256 electropherograms is classified by differences in sequences of two bases adjacent to the restriction enzyme recognition sites of the DNA fragments, and the 256 electropherograms are employed as fingerprints.

25. A method of analysis or assay for nucleotides according to claim 24, wherein the first labeled DNA probes are labeled by biotin.

26. A method of analysis or assay for nucleotides according to claim 25, wherein the second labeled DNA probes are labeled by a fluorophore.

27. A method of analysis or assay for nucleotides which comprises:

(1) digesting a sample DNA with a restriction enzyme to obtain DNA fragments;

(2) introducing a first and a second oligomer having known sequences into the DNA fragments at the 3' and 5' termini thereof, respectively;

(3) dividing a solution containing the DNA fragments into sixteen first vessels;

(4) performing a complementary strand synthesis in each of the sixteen first vessels, respectively, using different kinds of first labeled DNA probes having all possible sixteen combinations of two bases out of A, C, G and T at the 3' termini thereof, the first labeled DNA probes being complementary to the introduced oligomer or to a part of the recognition sequence recognized by said restriction enzyme, thereby extending the complementary strand of the first labeled DNA probes;

(5) removing non-reacted substances in the solutions in each of the sixteen first vessels of step (4), respectively, and, by elevating the temperature of the solution, liberating the DNA fragments from the hybrids of the complementary strand synthesis and recovering the DNA strand extended by the complementary strand synthesis in step (4), in each of the sixteen first vessels;

(6) performing a complementary strand synthesis in a second vessel containing the recovered DNA strand extended by the complementary strand synthesis from each of the sixteen first vessels, using a different kind of second labeled DNA probes different from the first labeled DNA probes, the second labeled DNA probes having all possible sixteen combinations of two bases out of A, C, G and T at the 3' termini thereof, the second labeled DNA probes being complementary to the introduced oligomer or to a part of the recognition sequence recognized by said restriction enzyme, thereby extending the complementary strand of the second labeled DNA probes, wherein the second labeled DNA probes are labeled with fluorophores having different emission wavelengths; and (7) obtaining 256 electropherograms by electrophoresis of the second labeled DNA probes extended by said complementary strand synthesis in the second vessel; wherein each of the 256 electropherograms is classified by differences in sequences of two bases adjacent to restriction enzyme recognition sites of the DNA fragments, and the 256 electropherograms are employed as fingerprints.

28. A method of analysis or assay for nucleotides which comprises:

(1) digesting a sample DNA with a restriction enzyme to obtain DNA fragments;

(2) introducing a first and a second oligomer having known sequences into the DNA fragments at the 3' and 5' termini thereof, respectively;

(3) dividing a solution containing the DNA fragments into sixteen first vessels;

(4) performing a complementary strand synthesis in each of the sixteen first vessels, respectively, using a different kind of first labeled DNA probes having all possible sixteen combinations of two bases out of A, C, G and T at the 3' termini thereof, the first labeled DNA probes being complementary to the introduced oligomer or to a part of the recognition sequence recognized by said restriction enzyme, thereby extending the complementary strand of the first labeled DNA probes;

(5) removing non-reacted substances in the solution in each of the sixteen first vessels of step (4), respectively, and, by elevating the temperature of the solution, liberating the DNA fragments from the hybrids of the complementary strand synthesis and recovering the DNA strand extended by the complementary strand synthesis in step (4), in each of the sixteen first vessels;

(6) dividing a solution containing the recovered DNA strand extended by the complementary strand synthesis from each of the sixteen first vessels into four second vessels;

(7) performing a complementary strand synthesis in each of the second four vessels, using second labeled DNA probes different from the first labeled DNA probes, the second labeled DNA probes having all possible sixteen combinations of two bases out of A, C, G and T at the 3' termini thereof, the second labeled DNA probes being complementary to the introduced oligomer or to a part of the recognition sequence recognized by said restriction enzyme, thereby extending the complementary strand of the second labeled DNA probes, wherein the second labeled DNA probes are labeled with fluorophores having four different emission wavelengths; and (8) obtaining 256 electropherograms by electrophoresis of the second labeled DNA probes extended by said complementary strand synthesis in the second four vessels; wherein each of the 256 electropherograms is classified by differences in sequences of two bases adjacent to restriction enzyme recognition sites of the DNA fragments, and the 256 electropherograms are employed as fingerprints.

* * * * *